(12) United States Patent
Jenkins

(10) Patent No.: US 9,023,860 B2
(45) Date of Patent: May 5, 2015

(54) PRO-DRUGS FOR CONTROLLED RELEASE OF BIOLOGICALLY ACTIVE COMPOUNDS

(75) Inventor: Thomas E. Jenkins, Half Moon Bay, CA (US)

(73) Assignee: Signature Therapeutics, Inc., Palo Alto, CA (US)

( * ) Notice: Subject to any disclaimer, the term of this patent is extended or adjusted under 35 U.S.C. 154(b) by 1167 days.

(21) Appl. No.: 12/324,383

(22) Filed: Nov. 26, 2008

(65) Prior Publication Data

US 2009/0137618 A1 May 28, 2009

Related U.S. Application Data

(60) Provisional application No. 60/990,184, filed on Nov. 26, 2007, provisional application No. 60/992,581, filed on Dec. 5, 2007.

(51) Int. Cl.
*C07D 489/04* (2006.01)

(52) U.S. Cl.
CPC .................................... *C07D 489/04* (2013.01)

(58) Field of Classification Search
CPC .. C07D 489/00; C07D 489/02; C07D 489/04; C07D 489/06; C07D 489/08; C07D 489/09; C07D 489/10; C07D 489/12; A61K 47/183; A61K 47/48238; A61K 47/48246
See application file for complete search history.

(56) References Cited

U.S. PATENT DOCUMENTS

| | | |
|---|---|---|
| 3,927,036 A | 12/1975 | Lee |
| 2004/0063628 A1 | 4/2004 | Piccariello et al. |
| 2005/0002895 A1 | 1/2005 | Corcoran |
| 2005/0080012 A1 | 4/2005 | Mickle et al. |
| 2008/0207668 A1 | 8/2008 | Moncrief |

FOREIGN PATENT DOCUMENTS

| | | |
|---|---|---|
| CA | 2497195 | 6/2003 |
| EP | 1501352 | 2/2005 |
| EP | 2046393 | 4/2009 |
| WO | WO 03051113 | 6/2003 |
| WO | WO 03072046 | 9/2003 |
| WO | WO 2004082620 | 9/2004 |
| WO | WO 2006017351 | 2/2006 |
| WO | WO 2007140272 | 12/2007 |
| WO | WO 2008101187 | 8/2008 |
| WO | WO 2008101202 | 8/2008 |

OTHER PUBLICATIONS

Uneyama, Fundamentals in Organic Fluorine Chemistry, 2006, pp. 10-15.*

Baillon et al. "Fluorinated Analogues of Spermidine as Substrates of Spermine Synthase" Eur. J. Biochem. 176(2): 237-242.
Bundgaard et al. (1989) "A Novel Solution-Stable, Water-Soluble Prodrug Type for Drugs Containing a Hydroxyl or an NH-Acidic Group" J. Med. Chem. 32(12):2503-2507.
De Groot, et al. (2000) "Synthesis and Biological Evaluation of 2'-Carbamate-Linked and 2'-Carbonate-Linked Prodrugs of Paclitaxel: Selective Activation by the Tumor-Associated Protease Plasmin" J. Med. Chem. 43 (16):3093-3102.
Kovach (1975) "Amino Acid Esters of Phenolic Drugs as Potentially Useful Prodrugs" J. Pharm. Sci. 64(6):1071-1072.
Page et al. (1986) "Stereochemical Studies. Part 112: Geometrical Dependence of Intramolecular Catalysis in the Hydrolysis and Aminolysis of Aryl Esters" J. Chem. Soc. Perkin. Trans. 2:867-871.
Saari et al. (1990) "Cyclization-Activated Prodrugs. Basic Cabamates of 4-Hdroxyanisole"Journal of Medicinal Chemistry 33(1):97-101.
Testa (Ed.) "Chapter 8: The hydrolysis of carboxylic acid ester prodrugs" Hydrolysis in Drug and Prodrug Metabolism, Verlag Helvetica Chimica Acta, 419-514.
Thomsen et al. (1994) "Evaluation of Phenyl Carbamates of Ethyl Diamines as Cyclization-Activated Prodrug Forms for Protecting Phenols against First-Pass Metabolism" Int. J. Pharma. 112:143-152.
Dhareshwar and Stella (2007) Biotechnology: Pharmaceutical Aspects: Prodrugs of Alcohols and Phenols Springer New York, vol. 5 (Part 3.2):63-99.
Fredholt Thomsen et al. (1993) "Cyclization-Activated Phenyl Carbamate Prodrug Forms for Protecting Phenols against First-Pass Metabolism" Int. J Pharm. 91:39-49.
Gomes et al. (2007) "Cyclization-Activated Prodrugs" Molecules 12:2484-2506.
Hay et al. (1968) "Catalysis by Aromatic Aldehydes and Carbon Dioxide of the Hydrolysis of the P-Nitrophenyl Esters of L-Leucine, Glycine, and L-B-Phenylalanine" Hydrolysis of Nitrophenyl Esters: 155-169.
Jensen et al. (1991) "Water-Soluble Aminoalkylbenzoate Esters of Phenols as Prodrugs: Synthesis, Enzymatic Hydrolysis and Chemical Stability of Paracetamol Esters" Acta. Pharm. Nord. 3(1):31-40.
Valters, (1982) "The electronic and steric effects in heterolytic intramolecular cyclisation reactions" Russian Chemical Reviews 51(8): 788-801.
Vigroux et al. (1995) "Cyclization-Activated Prodrugs: N-(Substituted 2-Hydroxyphenyl and 2-Hydroxypropyl) Carbamates Based on Ring-Opened Derivatives of Active Benzoxazolones and Oxazolidinones as Mutual Prodrugs of Acetaminophen" J. Med. Chem. 38:3983-3994.
Wermuth (1996) "Designing Prodrugs and Bioprecursors I: Carrier Prodrugs," The Practice of Medicinal Chemistry, Academic, London: 671-696.
Patani & Lavoie (1996) "Bioisosterism: A Rational Approach in Drug Design" Chem. Rev. 96(8):3147-3176.

* cited by examiner

*Primary Examiner* — Christina Bradley
(74) *Attorney, Agent, or Firm* — Carol L. Francis; Khin K. Chin; Bozicevic, Field & Francis LLP

(57) ABSTRACT

Pro-drugs containing an electron withdrawing substituent, as defined in the specification, are useful in a method for providing a patient with post administration-activated, controlled release of a biologically active compound.

21 Claims, No Drawings

PRO-DRUGS FOR CONTROLLED RELEASE OF BIOLOGICALLY ACTIVE COMPOUNDS

This application claims the benefit of U.S. provisional patent application No. 60/990,184 filed on Nov. 26, 2007 and U.S. provisional patent application No. 60/992,581 filed on Dec. 5, 2007, the contents of which are incorporated herein in their entirety.

The present invention relates to novel pro-drugs. More particularly, it relates to pro-drugs capable of providing controlled release of biologically active compounds, to a process for making the pro-drugs, to novel intermediates useful in the process, to a pharmaceutical composition containing the pro-drugs and to the use of the pro-drugs in therapy.

Biologically active compounds are often delivered to patients in the form of a pro-drug. Typically, in a pro-drug, a polar functional group (for example, a carboxylic acid, an amino group, a phenol group, or a sulfhydryl group) of the active compound is masked by a promoiety, which is labile under physiological conditions. Accordingly, pro-drugs are usually transported through hydrophobic biological barriers such as membranes and may possess superior physicochemical properties in comparison to the parent drug. Often pro-drugs can optimize bioavailability, improve dosage consistency and improve patient compliance (e.g., by reducing dosing frequency). Pro-drugs are usually non-toxic and are ideally selectively cleaved at the locus of drug action. Preferably, cleavage of the promoiety occurs rapidly and quantitatively with the formation of non-toxic by-products (i.e., the hydrolyzed promoiety).

Pro-drugs as described above are capable of providing patients with safe and effective treatment if the patients follow the directions given by the attending physician. Unfortunately human patients do not always follow the directions that they have been given. They may accidentally take an overdose of the pro-drug, or deliberately abuse it, for example by taking an overdose, by injecting or inhaling it, or by using readily available household chemicals (like vinegar or baking soda) to obtain the active drug from the pro-drug. Abuse is a particular concern with pro-drugs of recreational or addictive drugs, like amphetamines and opioids.

It would be desirable to have a pro-drug that has built-in control, so that it is difficult to use the pro-drug other than in the way it is intended.

A new way has now been found for configuring pro-drugs of biologically active compounds having a hydrogen atom bonded to an aryloxy, arylthio or arylamino group, that affords controlled release of the compounds.

According to one aspect, the present invention provides a method of providing a patient with post administration-activated, controlled release of a biologically active compound having a hydrogen atom bonded to an aryloxy, arylthio or arylamino group, which comprises administering to said patient a corresponding compound (pro-drug in accordance with the present invention) in which the hydrogen atom has been substituted with an acyl leaving group bearing a nitrogen nucleophile that is protected with a proton or an enzymatically-cleavable moiety, said acyl leaving group also bearing at least one electron-withdrawing substituent positioned beta to the protected nitrogen nucleophile, the configuration of the acyl leaving group and nitrogen nucleophile being such that, upon deprotonation or enzymatic cleavage of the cleavable moiety, the nitrogen nucleophile is capable of liberating the compound from the acyl leaving group by an intramolecular cyclization-release reaction so as to provide the patient with controlled release of the compound.

A particular feature of the pro-drug is the at least one electron-withdrawing substituent positioned beta to the protected nitrogen nucleophile. The presence of the electron-withdrawing substituent lowers the basicity of the nitrogen nucleophile, such that it is less susceptible to protonation at physiological pH. As such, the cyclization-release reaction is facilitated resulting in enhanced release of biologically active compound at physiological pH.

In one embodiment, the nitrogen nucleophile is protected with a proton (i.e., the corresponding compound is an acid addition salt). In use of the corresponding compound, the proton is removed (the compound is deprotonated) at physiological pH.

In another embodiment, the nitrogen nucleophile is protected with an enzymatically-cleavable moiety. In this embodiment, the corresponding compound provides post administration-activated, controlled release of the biologically active compound, because it requires enzymatic cleavage to initiate release of the compound, and because the rate of release of the compound depends upon both the rate of enzymatic cleavage and the rate of cyclisation. Accordingly, the pro-drug can have reduced susceptibility to accidental overdosing or abuse, whether by deliberate overdosing, administration through an inappropriate route, such as by injection, or by chemical modification using readily available household chemicals. The pro-drug is configured so that it will not provide excessively high plasma levels of the active drug if it is administered inappropriately, and cannot readily be decomposed to afford the biologically active compound other than by enzymatic cleavage.

The enzyme capable of cleaving the enzymatically-cleavable moiety may be a peptidase—the enzymatically-cleavable moiety being linked to the nucleophilic nitrogen through an amide (e.g., a peptide: —NHCO—) bond. In some embodiments, the enzyme is a digestive enzyme such as, a pancreatic or brush border enzyme, such as those involved in peptide hydrolysis. Examples include pepsin, trypsin, chymotrypsin, colipase, elastase, aminopeptidase N, aminopeptidase A, dipeptidylaminopeptidase IV, tripeptidase or enteropeptidase. Accordingly, in one embodiment of the method, the corresponding compound is administered orally to the patient.

The enzyme-cleavable moiety linked to the nitrogen nucleophile through an amide bond may be, for example, a residue of an amino acid or a peptide, or an (alpha) N-acyl derivative of an amino acid or peptide (for example an N-acyl derivative of a pharmaceutically acceptable carboxylic acid, such as an N-acetyl or benzoyl derivative). The peptide may contain, for example, up to 10 amino acid residues. For example, it may be a dipeptide or tripeptide. Each amino acid is an L-amino acid. Examples of naturally occurring amino acids are alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine. Accordingly, examples of enzyme-cleavable moieties include residues of the L-amino acids listed hereinabove and the N-acetyl or benzoyl derivatives thereof, and dipeptides and tripeptides formed from two or three of the L-amino acids listed hereinabove, and the N-acetyl or benzoyl derivatives thereof.

The cyclic group formed when the biologically active compound is released is conveniently pharmaceutically acceptable, in particular a pharmaceutically acceptable cyclic urea, carbamate or thiocarbamate. It will be appreciated that cyclic ureas in particular are generally very stable and have low toxicity.

In one specific example of the invention, the acyl leaving group bearing a protected nitrogen nucleophile is a group of formula

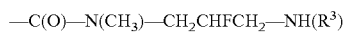
—C(O)—N(CH$_3$)—CH$_2$CHFCH$_2$—NH(R$^3$)

wherein R$^3$ is an enzyme-cleavable moiety linked to the NH group through an amide bond, such as a residue of an amino acid. When the N—R$^3$ amide bond is cleaved enzymatically, a nitrogen nucleophile (—NH$_2$) is freed, and this cyclises back onto the carbonyl group, forming a cyclic urea and releasing the biologically active compound. The presence of the fluorine atom, which is an electron-withdrawing substituent, reduces the susceptibility of the nitrogen nucleophile (—NH$_2$) to protonation, and thus facilitates the cyclization-release reaction under physiological conditions.

Generally, the acyl leaving group bearing a protected nitrogen nucleophile may be any group capable of forming a cyclic urea, carbamate or thiocarbamate when the biologically active compound is displaced by the nitrogen nucleophile. Accordingly, the acyl leaving group bearing a protected nitrogen nucleophile may be, for example, a group of formula

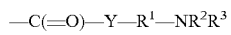
—C(=O)—Y—R$^1$—NR$^2$R$^3$ or a pharmaceutically acceptable salt thereof, in which:

Y is O, S or NR$^4$;

R$^1$ comprises an unbranched, branched or ring-containing (2-8C) alkylene group having from 2 to 4 carbon atoms in a chain linking Y to NR$^2$R$^3$ and at least one electron withdrawing substituent positioned beta to NR$^2$R$^3$;

R$^2$ is hydrogen or (1-4C)alkyl;

R$^3$ is a hydrogen atom or a residue of an amino acid or a peptide, or an N-acyl derivative of an amino acid or peptide; and R$^4$ is hydrogen or (1-4C)alkyl.

It will be appreciated that when R$^3$ is hydrogen, the acyl leaving group may be in the form of the free base, or a pharmaceutically acceptable acid addition salt that may be represented by the formula

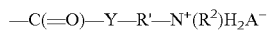
—C(=O)—Y—R'—N$^+$(R$^2$)H$_2$A$^-$ in which A$^-$ represents a pharmaceutically acceptable anion. The free base is useful in the preparation of the acid addition salt, and is accordingly provided with the present invention.

An example of a value for Y is NR$^4$.

An example of a value for R$^4$ is methyl.

R$^1$ comprises an unbranched, branched or ring-containing (2-8C)alkylene group having from 2 to 4 carbon atoms in a chain linking Y to NR$^2$R$^3$.

The group represented by R$^1$ may be, for example, an alkylene, cycloalkylene, alkylcycloalkylene or cycloalkylalkylene or alkylcycloalkylalkylene group. It may bear one or more substituents in addition to the one or more electron withdrawing substituents positioned beta to NR$^2$R$^3$.

Examples of values for an unbranched, branched or ring-containing (2-8C)alkylene group having from 2 to 4 carbon atoms in a chain linking Y to NR$^2$R$^3$ are: 1,3-propylene and 2,3-butylene.

The at least one electron withdrawing substituent may be positioned on an atom in the chain connecting Y with NR$^2$R$^3$, or on an atom connected to that chain.

The number of electron withdrawing substituents positioned beta to NR$^2$R$^3$ may be, for example, 1, 2, 3 or more. The number will depend upon the particular electron withdrawing substituent, or substituents, chosen.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylamincarbonyl or arylaminocarbonyl group), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the at least one electron withdrawing substituents may be selected independently from these.

Examples of an acyl leaving group bearing at least one electron withdrawing group are: —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$_a$R$_b$)—; —CH$_2$CH(C(O)OR$_c$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O)NR$_d$R$_e$)—; —CH$_2$CH$_2$CH(C(O)OR$_f$)—; and —CH$_2$CH$_2$CH(C(O)OH)—, in which R$_a$, R$_b$, R$_d$ and R$_e$ each independently represents hydrogen or (1-6C)alkyl, such as methyl or ethyl, and R$_c$ and R$_f$ each independently represents (1-6C)alkyl, such as methyl or ethyl.

It will be appreciated that the group R$^1$ may contain one or more chiral centres. The present invention contemplates the group R$^1$ being in any of the possible stereoisomeric forms.

An example of a value for R$^2$ is hydrogen.

In one embodiment, the at least one electron withdrawing substituent is a fluorine atom.

In one embodiment, the acyl leaving group bears one, two or three fluorine substituents positioned beta to the protected nitrogen nucleophile.

Examples of an acyl leaving group bearing one, two or three fluorine substituents positioned beta to the protected nitrogen nucleophile are: —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; and —CH$_2$CH$_2$CH(CH$_2$F)—.

An example of a value for R$^2$ is hydrogen.

Accordingly, in one embodiment, Y is NR$^4$, R$^4$ is methyl and R$^2$ is hydrogen.

A— may be any pharmaceutically acceptable anion (i.e. an anion derived from a pharmaceutically acceptable acid). Examples of pharmaceutically acceptable anions include halide ions, such as chloride, and sulfate.

R$^3$ may be, for example, a hydrogen atom or a residue of an L-amino acid, such as an L-amino acid selected from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine; a residue of a dipeptide or tripeptide composed of two or three L-amino acid residues selected independently from alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine and valine; or a residue of an N-acyl derivative thereof.

The acyl group in an N-acyl group can be, for example, a residue of a pharmaceutically acceptable carboxylic acid, such as acetic acid or benzoic acid.

In one embodiment, $R^3$ is a hydrogen atom.

In another embodiment, $R^3$ is a residue of an L-amino acid or a dipeptide or tripeptide composed of two or three L-amino acids, or an N-acetyl or benzoyl derivative thereof.

Examples of particular values for $R^3$ are the L-forms of arginine, N-acetylarginine, N-glycinylarginine, N-acetylglycinylarginine, alanine, phenylalanine, N-acetylalanine, asparagine, N-acetylasparagine, aspartic acid, N-acetylaspartic acid, lysine, N-acetyllysine, leucine, N-acetylleucine, glutamic acid, tyrosine and N-acetyltyrosine.

In a particular embodiment, $R^3$ is a residue of L-leucine or L-arginine, or an N-acetyl or benzoyl derivative thereof.

The biologically active compound may be any compound having a hydrogen atom bonded to an aryloxy, arylthio or arylamino group. Accordingly, in one embodiment, the pro-drug may be a compound of the general formula (I):

X—C(=O)—Y—R$^1$—NR$^2$R$^3$     (I)

or a pharmaceutically acceptable salt thereof, in which X represents a biologically active compound having a phenol, thiophenol or aniline group in which the hydrogen atom of the aryl hydroxyl, thiol or amino group is replaced by a covalent bond to —C(=O)—Y—R$^1$—NR$^2$R$^3$.

However, the control of release of the biologically active compound built-in to the pro-drug is of special importance for compounds that are recreational or addictive drugs, like those of the opioids that bear a phenol group—the phenolic opioids.

Examples of phenolic opioids include buprenorphine, dihydroetorphine, diprenorphine, etorphine, hydromorphone, levorphanol, morphine, nalmefene, naloxone, N-methylnaloxone, naltrexone, N-methylnaltrexone and oxymorphone. Particular mention is made of hydromorphone, morphine and oxymorphone.

Accordingly, the biologically active compound is preferably a phenolic opioid, such as one of those listed by way of example hereinabove. In a preferred embodiment, therefore, X is a residue of a phenolic opioid in which the hydrogen atom of the phenol group is replaced by a covalent bond to —C(=O)—Y—R$^1$—NR$^2$R$^3$.

Phenolic opioids fall into two sub-groups, depending upon whether they function as an agonist or antagonist.

The phenolic opioids are properly used for the treatment of pain. Examples of agonists include buprenorphine, dihydroetorphine, etorphine, hydromorphone, levorphanol, morphine and oxymorphone. The antagonists block the function of the agonists, and are therefore used to counter effects of the agonists when these are undesired. Examples of phenolic opioid antagonists include diprenorphine, naltrexone, naloxone, nalmefene, N-methyl naloxone and N-methylnaltrexone. The phenolic antagonists that contain a quaternary ammonium group, such as N-methyl naloxone and N-methylnaltrexone, are incapable of crossing the blood brain barrier, and are therefore useful for antagonising the peripheral side effects of phenolic opioid agonists, such as constipation.

In another aspect, the present invention provides a compound of formula (I), or a pharmaceutically acceptable salt thereof, in which X is a residue of a phenolic opioid selected from buprenorphine, dihydroetorphine, diprenorphine, etorphine, hydromorphone, levorphanol, morphine, nalmefene, naloxone, N-methyl naloxone, naltrexone, N-methylnaltrexone and oxymorphone. In one embodiment, X is a residue of a phenolic opioid selected from hydromorphone, morphine, and oxymorphone.

For example, when X is a residue of hydromorphone, the pro-drug may be represented by the formula (Ia)

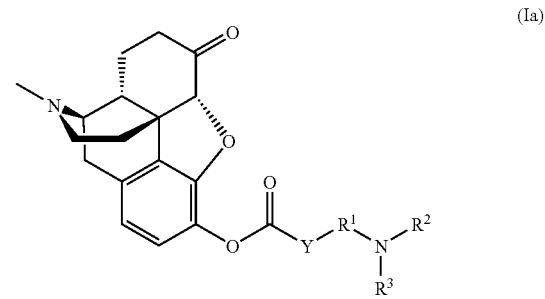

In the compounds of formula (I), (Ia), etc., each of Y, $R^1$, $R^2$, and $R^3$ may have any of the meanings given hereinabove.

In one embodiment, the pro-drug is a compound of formula (Ia) or a pharmaceutically acceptable salt thereof, in which Y is N(CH$_3$), $R^1$ is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$_a$R$_b$)—; —CH$_2$CH(C(O)OR$_c$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O)NR$_d$R$_e$)—; —CH$_2$CH$_2$CH(C(O)OR$_f$)—; and —CH$_2$CH$_2$CH(C(O)OH)—, in which R$_a$, R$_b$, R$_d$ and R$_e$ each independently represents hydrogen or (1-6C)alkyl, such as methyl or ethyl, and R$_c$ and R$_f$ each independently represents (1-6C)alkyl, such as methyl or ethyl, $R^2$ is hydrogen and $R^3$ is hydrogen or a residue of an L-amino acid, or an N-acetyl L-amino acid, such as L-leucine, N-acetyl-L-leucine, L-arginine or N-acetyl-L-arginine.

An example of a compound of formula (Ia) is the compound of formula:

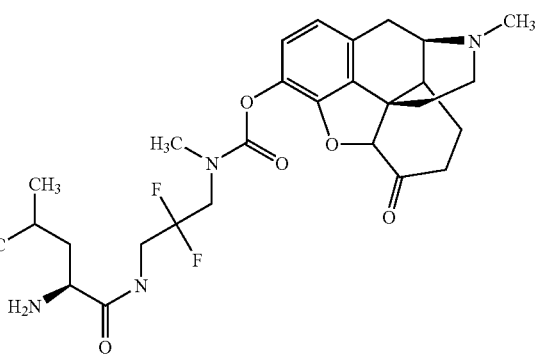

The pro-drugs may be prepared from readily available starting materials by peptide coupling. Thus, when the pro-drug is a compound of formula (I), it may be prepared by a process, which comprises:

a) reacting a compound of formula (II)

X—C(=O)—Z     (II)

or a protected derivative thereof, in which Z represents a leaving atom or group, with a compound of formula (III)

$$H—Y—R^1—NR^2R^3 \quad (III)$$

or a protected derivative thereof; or b) reacting a compound of formula (IV)

$$X—C(=O)—Y—R^1—NHR \quad (IV)$$

or a protected derivative thereof, with a compound of formula (V)

$$HR^3 \quad (V)$$

or a protected derivative thereof, or reactive derivative of said compound of formula (V) or protected derivative thereof;

followed, if desired, by N-acylating an amino group in $R^3$ to afford another compound of formula (I);

removing any protecting groups and, if desired, forming a pharmaceutically acceptable salt.

Each of steps a) and b) and the optional N-acylation step involves peptide coupling, which is well known. Peptide coupling comprises reacting a carboxylic acid, or a reactive derivative thereof, with an amine. Where appropriate, other reactive amino groups present in the starting materials may be protected with a suitable protecting group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethane-sulfonyl ("SES"), trityl and substituted trityl groups, allyloxycarbonyl, 9-fluorenylmethyloxycarbonyl ("FMOC"), and nitro-veratryloxycarbonyl ("NVOC").

In step a), the leaving atom or group represented by X may be, for example p-nitrophenoxy.

N-acyl derivatives of the compounds of formula (I) may conveniently be prepared by acylating a corresponding compound of formula (I) using an appropriate acylating agent, for example an anhydride, such as acetic anhydride (to prepare an N-acetyl compound) or an acid halide. The reaction is conveniently performed in the presence of a non-reactive base, for example a tertiary amine, such as triethylamine. Convenient solvents include amides, such as dimethyl formamide. The temperature at which the reaction is performed is conveniently in the range of from 0 to 100° C., such as at ambient temperature.

The starting materials used in steps a) and b) may be prepared using methods analogous to methods known in the art, for example by coupling amino acids (protected as appropriate) to form peptides. Thus, compounds of formula (III) may be prepared by reacting a compound of formula (VI)

$$H—Y—R^1—NHR^2 \quad (VI)$$

or a protected derivative thereof (for example protected on Y, such as with t-butoxycarbonyl when Y is $NR^4$), with a compound of formula (V) or a protected derivative thereof, or reactive derivative of said compound of formula (V) or protected derivative thereof.

Certain of the intermediates disclosed herein, particularly intermediates of formula (III) are believed to be novel. The present invention also provides those of the intermediates that are novel.

According to another aspect, therefore, the present invention provides a compound of formula (III)

$$H—Y—R^1—NR^2R^3 \quad (III)$$

or a protected derivative thereof, or a salt thereof; in which:

Y is O, S or $NR^4$;

$R^1$ is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$_a$R$_b$)—; —CH$_2$CH(C(O)OR$_c$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O)NR$_d$R$_e$)—; —CH$_2$CH$_2$CH(C(O)OR$_f$)—; and —CH$_2$CH$_2$CH(C(O)OH)—, in which $R_a$, $R_b$, $R_d$ and $R_e$ each independently represents hydrogen or (1-6C)alkyl, such as methyl or ethyl, and $R_c$ and $R_f$ each independently represents (1-6C)alkyl, such as methyl or ethyl;

$R^2$ is hydrogen or (1-4C)alkyl;

$R^3$ is hydrogen or a residue of an amino acid or a peptide, or an N-acyl derivative of an amino acid or peptide; and $R^4$ is hydrogen or (1-4C)alkyl.

A protected derivative of the compound of formula (I) may bear a protecting group on Y (instead of the hydrogen atom), or on one or more amino groups in $R^3$. When Y represents a group of formula $NR^4$, convenient protecting groups include alkyloxycarbonyl and aryloxycarbonyl groups, such as benzyloxycarbonyl (CBz). Convenient protecting groups for one or more amino groups in $R^3$ include formyl, acetyl, trifluoroacetyl, benzyl, benzyloxycarbonyl ("CBZ"), tert-butoxycarbonyl ("Boc"), trimethylsilyl ("TMS"), 2-trimethylsilylethane-sulfonyl ("SES"), trityl and substituted trityl groups, allyloxycarbonyl, 9-fluorenylmethyloxycarbonyl ("FMOC"), and nitro-veratryloxycarbonyl ("NVOC").

Conveniently the compound and its pharmaceutically acceptable salts are administered to the patient in a pharmaceutical composition.

According to another aspect therefore, the present invention provides a pharmaceutical composition, which comprises a compound of formula (I) or a pharmaceutically acceptable salt thereof, and a pharmaceutically acceptable carrier.

The compounds of the invention may be formulated for administration by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably, for injection or infusion, the compositions will be sterile and in a suitable solution or suspension form. Such compositions form a further aspect of the invention.

The compound of formula (I) is configured to release the biologically active compound when administered orally to a patient. Accordingly, in one embodiment it is formulated in a pharmaceutical composition adapted for oral administration.

The pro-drugs according to the present invention afford a biologically active compound in vivo, and accordingly are useful in the treatment of the same conditions as the biologically active compound.

Accordingly, the compounds of the present invention in which X represents a residue of a phenolic opioid which is an agonist are useful in the treatment (including prophylaxis) of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The compounds of the present invention in which X represents a residue of a phenolic opioid which is an antagonist are useful in the treatment of patients requiring opioid antagonist treatment, for example a patient that has received an inappropriate dose of an agonist, or has become dependent on an agonist. The compounds of the present invention in which X represents a residue of a phenolic opioid which is a peripheral antagonist are useful for treating patients suffering from the peripheral side effects of agonist treatment, such as constipation.

The term "patient" as used herein includes humans, but also other mammals, such as livestock, zoo animals and companion animals.

According to another aspect therefor, the present invention provides a method of treating pain in a patient in need of treatment, which comprises administering an effective amount of the compound of formula (I) or a pharmaceutically acceptable salt thereof in which X is a residue of a phenolic opioid selected from buprenorphine, dihydroetorphine, etorphine, hydromorphone, levorphanol, morphine and oxymorphone.

The dose of the pro-drug administered to the patient will depend upon many different factors to be considered by the attending physician, including the age, weight and sex of the patient, and the nature of the condition being treated. In general, the pro-drug will be administered at a dose equivalent to that required to provide the patient with an effective amount of the biologically active agent. For example, when the pro-drug is a derivative of hydromorphone, it will be administered at a dose equivalent to administering free hydromorphone in the range of from about 0.02 mg/kg to about 0.5 mg/kg body weight. In one embodiment, the compound will be administered at a dose such that the level of opioid achieved in the blood is in the range of from about 0.5 ng/ml to about 10 ng/ml.

The following preparations and illustrative embodiments illustrate the invention.

Amino acids in depicted structures are intended to be natural L amino acids. Each structure can be any possible stereoisomer or any mixture thereof.

PREPARATION 1

Benzotriazol-1-ylmethyl-benzyl-methyl-amine

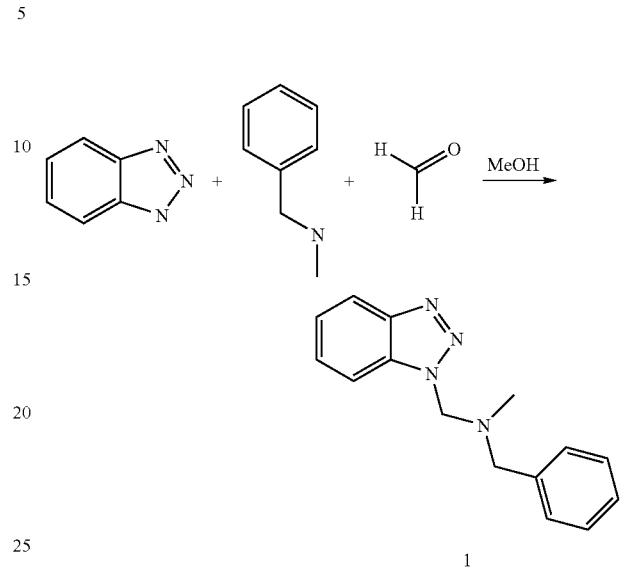

Benzotriazole (6 g, 50 mmol) and N-methylbenzylamine (10.57 ml, 55 mmol) were dissolved in methanol (MeOH) (25 ml) followed by drop wise addition of formaldehyde (4.9 ml, 37% in $H_2O$). The resulting mixture was heated at 50° C. for 15 h and cooled to ambient temperature. It was then diluted with diethyl ether ($Et_2O$) (100 ml), washed with saturated sodium chloride aqueous solution (brine) (2×70 ml) and dried over magnesium sulfate ($MgSO_4$) and concentrated. Upon further drying under reduced pressure, the material solidified to afford the depicted compound (13.2 g, 85%).

PREPARATION 2

3-(N-Benzyl-N-methylamino)-2,2-difluoropropionic Acid Methyl Ester

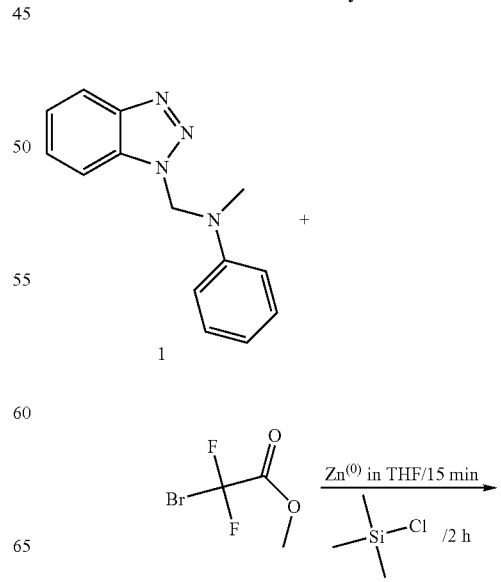

-continued

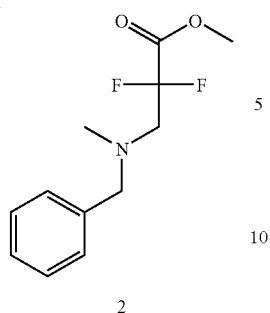

2

Chlorotrimethylsilane (TMSCl) (3.62 mL, 33.3 mmol) was added to a stirred suspension of zinc (Zn) dust (4.5 g, 65 mmol) in approx. 94 ml of anhydrous tetrahydrofuran (THF), followed by addition of methyl bromodifluoroacetate (22 mmol). The reaction mixture was stirred at ambient temperature for 15 min followed by addition of Preparation 1 in THF (32.5 mmol, 50 ml) to the stirred solution. The reaction mixture was stirred at ambient temperature for 2 h. The solid material was then filtered off. Volatiles were removed under reduced pressure. Residue was treated with 5% sodium bicarbonate ($NaHCO_3$) and ethyl acetate. The organic layer was dried with $MgSO_4$ and evaporated. The depicted product was isolated as an oil and used in the next step "as is".

PREPARATION 3

3-(N-Benzyl-N-methylamino)-2,2-difluoropropan-1-ol

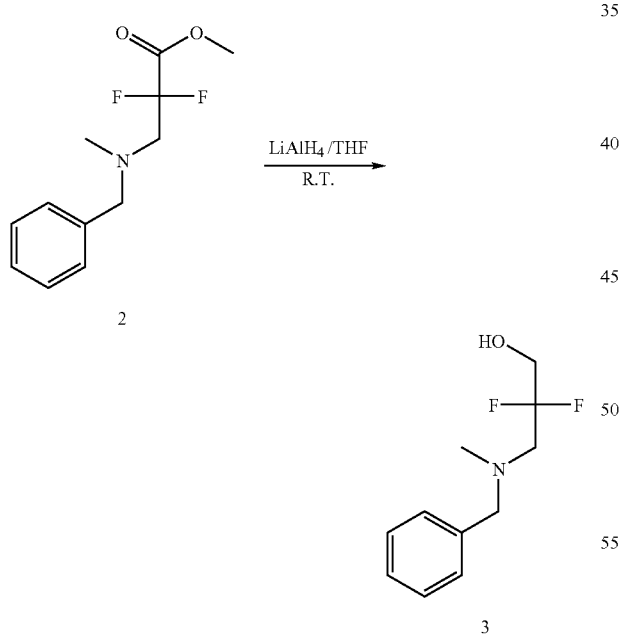

Preparation 2 was dissolved in approx. 300 ml of THF, cooled down to −20° C. followed by drop wise addition of 35 ml of lithium aluminium hydride ($LiAlH_4$) (2.5 M in THF). The reaction mixture was stirred 1 h at ambient temperature (R.T.) followed by addition of an extra 30 ml of $LiAlH_4$. The reaction mixture was kept at ambient temperature for 3 h, quenched by aqueous 1M sodium hydroxide (NaOH) (300 ml). The product was extracted with diethyl ether (3×200 ml). The ether layer was dried over $MgSO_4$ and evaporated to yield the depicted product as an oil.

PREPARATION 4

3-(N-methylamino)-2,2-difluoropropan-1-ol

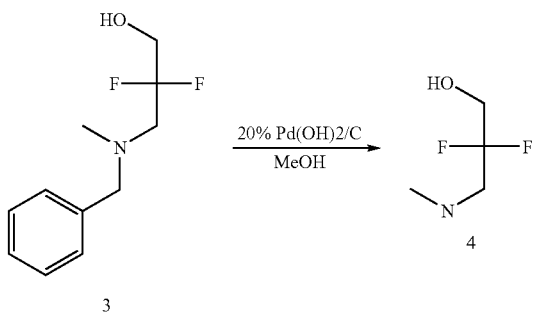

Preparation 3 (20 g crude) was dissolved in 150 ml of MeOH followed by addition of half teaspoon of 20% palladium hydroxide on carbon ($Pd(OH)_2/C$). Debenzylation was performed overnight at 75 PSI of hydrogen. Catalyst was filtered off and solvent was removed under reduced pressure to yield the depicted product as a crude oil (11.5 g, 100%).

PREPARATION 5

Carbobenzoxy-3-(N-methylamino)-2,2-difluoropropan-1-ol

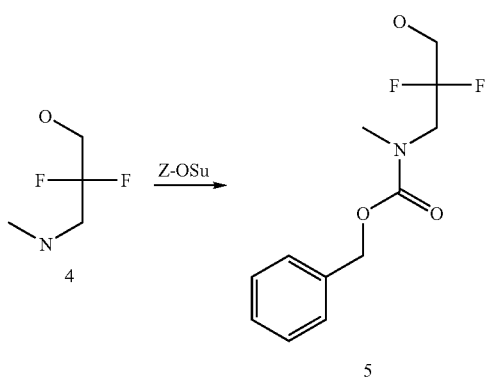

Preparation 4 (11.5 g, ~90 mmol) was transferred to a 500 ml round bottomed flask followed by addition of N-(benzyloxycarbonyloxy)succinimide (Z-OSu) (22.6 g, 90 mmol), triethylamine (TEA) (12 ml, 90 mmol) and 200 ml isopropanol. The reaction mixture was kept at 50° C. for 3 h. Solvent was removed under reduced pressure. The residue was purified by CombiFlash (hexane/ethyl acetate) to yield the depicted product as a clear oil (11.5 g, 48%).

PREPARATION 6

Carbobenzoxy-3-(N-methylamino)-2,2-difluoropropylphthalimide

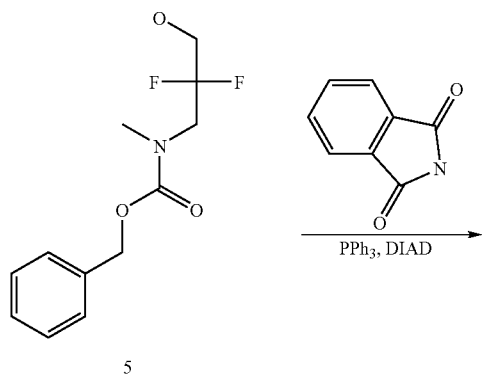

5

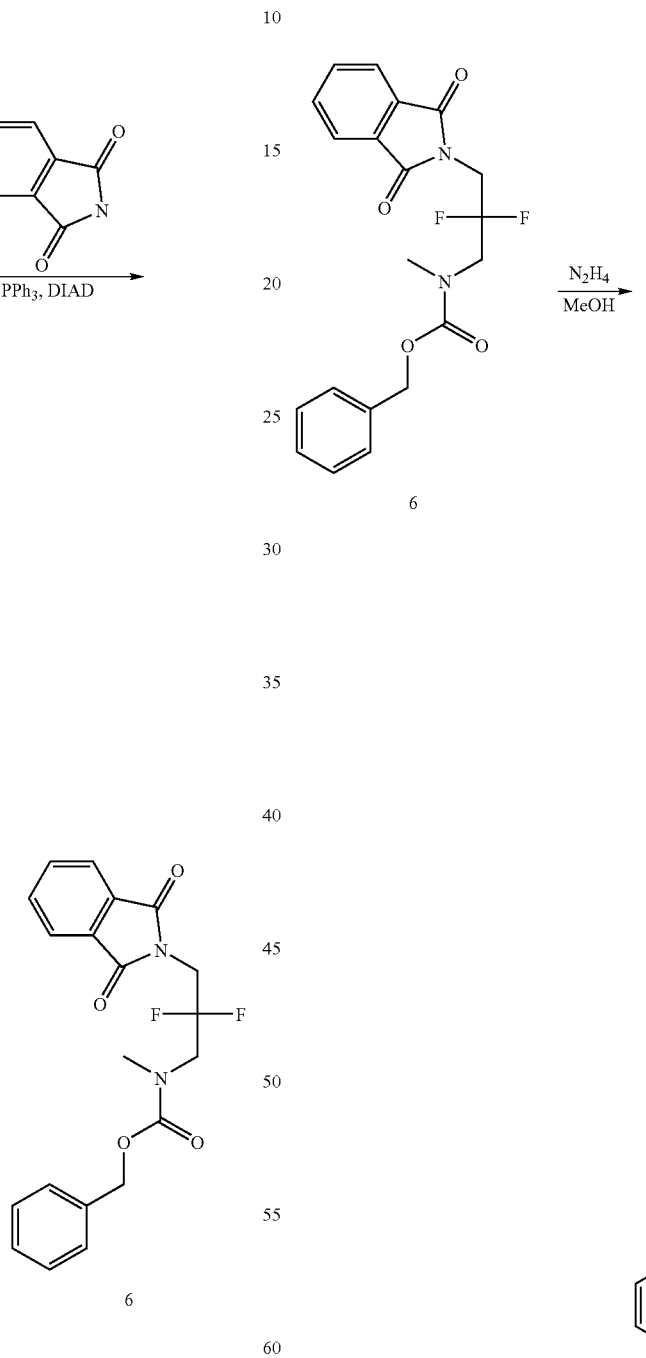

6

A portion of Preparation 5 (5 g, 19.3 mmol), phthalimide (3 g, 21 mmol) and triphenylphosphine (Ph₃P) (5.8 g, 22 mmol) were dissolved in 150 ml THF, cooled down to −30° C., followed by addition of diisopropyl azodicarboxylate (DIAD) (4.4 g, 22 mmol). The reaction mixture was stirred at ambient temperature overnight. Solvent was removed under reduced pressure. The crude product was purified on silica gel (CombiFlash, ethyl acetate/hexane), yielding the depicted product as a clear oil (6.3 g, 84%).

PREPARATION 7

Carbobenzoxy-3-(N-methylamino)-2,2-difluoropropylamine

7

Preparation 6 (6.3 g, 16.2 mmol) was dissolved in 50 ml of MeOH followed by addition of hydrazine (N2H₄) hydrate (2.5 g, 50 mmol). The mixture was stirred at 60° C. 2 h. Solid was filtered off. Volatiles were evaporated. Residue was purified by prep reverse phase HPLC (1.5 in.×300) to yield the depicted product (2.5 g, 62%).

PREPARATION 8

Carbobenzoxy-3-(N-methylamino)-2,2-difluoropropyl-N-Boc-amine

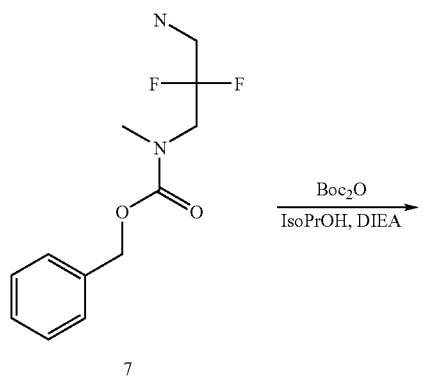

PREPARATION 9

3-(N-methylamino)-2,2-difluoropropyl-N-Boc-amine

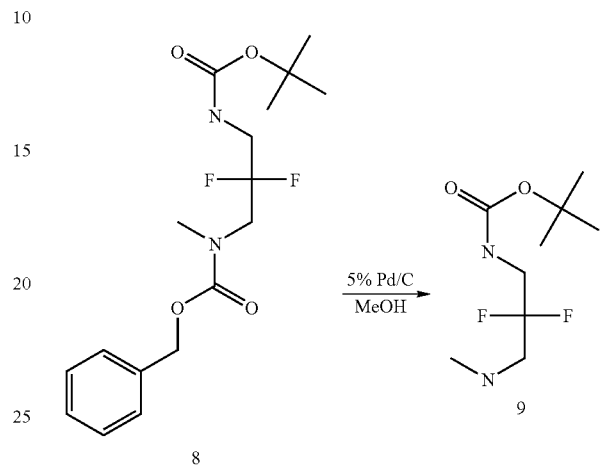

Preparation 8 (0.4 g, 1.1 mmol) was hydrogenated in 50 ml MeOH (30 min, 60 PSI) over 5% palladium on carbon (Pd/C). Catalyst was filtered off and solvent evaporated to yield the depicted product as a yellow oil (0.21 g, 82%).

PREPARATION 10

3-(4-Nitrophenyl)-hydromorphone Carbonate

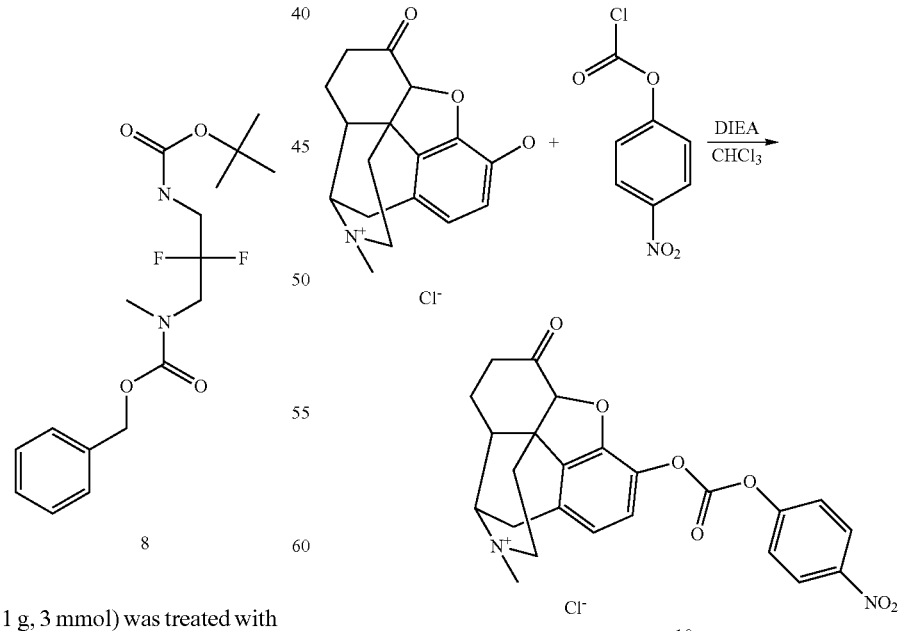

A portion of Preparation 7 (1.1 g, 3 mmol) was treated with di-tert-butyl dicarbonate (Boc₂O) (1 g, 4.8 mmol) in isopropanol (IsoPrOH) (10 ml) in the presence of 0.7 ml DIEA overnight at 50° C. The reaction mixture was diluted with ethyl acetate (50 ml). The organic layer was washed with water, brine, and dried over MgSO₄. The depicted product was purified by CombiFlash (hexane-ethyl acetate, yielding a yellow oil (0.4 g, 36%).

Hydromorphone hydrochloride (0.3 g, 0.92 mmol) and DIEA (0.16 ml, 0.92 mmol) were mixed in chloroform (CHCl₃) (5 ml) and sonicated in an ultrasound bath (1 h, ambient temperature) followed by addition of p-nitrophenyl chloroformate (0.19 g, 0.92 mmol). Sonication was repeated (1 h, ambient temperature). Conversion to p-nitrophenylcarbonate was monitored by LC MS. The solution of the depicted product was used "as is".

PREPARATION 11

Hydromorphone 3-(N-methyl-N-(3-t-butoxcarbonylamino-2,2-difluoro)propyl)carbamate

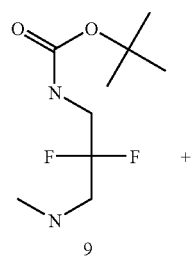

9

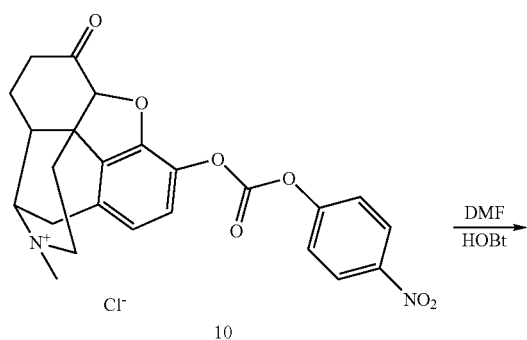

10

DMF
HOBt

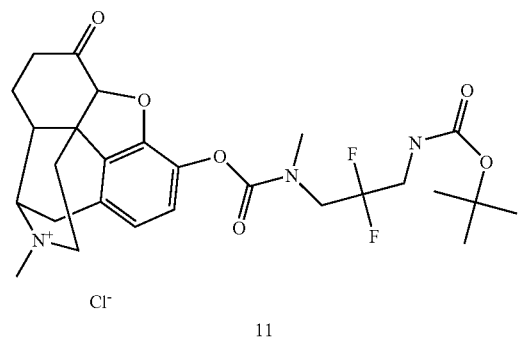

11

A solution of Preparation 10 was mixed with Preparation 9 (0.21 g, 0.92 mmol) followed by addition of 3 ml N,N-dimethylformamide (DMF) and 1-hydroxybenzotriazole (HOBt) (0.13 g, 0.92 mmol). The reaction mixture was stirred overnight. The reaction was monitored by LC MS. Chloroform was removed under reduced pressure (bath temperature below 30° C.). The residual solution was loaded on reverse phase HPLC RP-18 silica gel column (1.5 in.×300, water-acetonitrile, 0.1% TFA). Fractions containing the depicted product were collected and evaporated (bath temperature below 40° C.), yielding a colorless oil (~0.3 g, 51%).

PREPARATION 12

3-(N-Benzyl-N-methylamino)-2-fluoropropionic Acid Methyl Ester

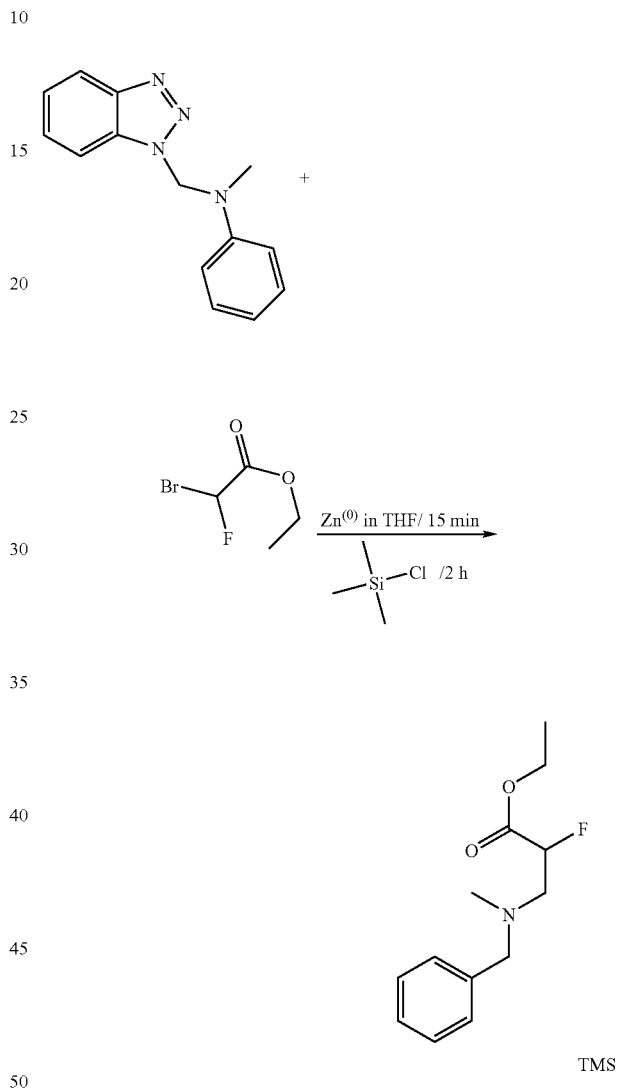

Cl (3.5 g, 32.4 mmol) was added to a stirred suspension of zinc dust (4.2 g, 65 mmol) in THF (80 mL), followed by addition of ethyl bromofluoroacetate (4 g, 21.6 mmol). The reaction mixture was stirred at ambient temperature for 15 min. A solution of Preparation 1 (8.1 g, 32.4 mmol) in 40 ml of THF was added slowly during a period of 10 min. The reaction was stirred at ambient temperature for 2 h and quenched by adding aqueous (aq.) potassium carbonate (K₂CO₃) (1M, 60 ml), and ethyl acetate (100 ml). The mixture was stirred vigorously for 10 min. After layer separation, the aqueous layer was extracted with ethyl acetate (50 ml). The combined organic phase from the extract was washed with brine (100 ml) and dried over sodium sulfate (Na₂SO₄) and concentrated. The concentrated crude material was purified by chromatography (CombiFlash, 40 g column, MeOH in dichloromethane (DCM) 0% to 12%) to afford the depicted product as a light-yellow oil (4.3 g, 84%).

PREPARATION 13

3-(N-Benzyl-N-methylamino)-2-fluoropropan-1-ol

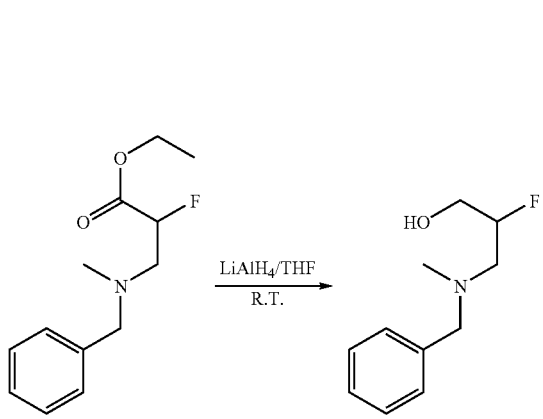 [SMILES: CCOC(=O)C(F)CN(C)Cc1ccccc1 ; CN(Cc1ccccc1)CC(F)CO]

Eighteen ml of LiAlH$_4$ solution (2 M, THF) was added drop wise to Preparation 12 (4.3 g, 18 mmol) in 80 ml of THF at −20° C. The reaction was then stirred at ambient temperature for 1 h and quenched by adding 1M NaOH solution until there was no bubbling. The mixture was diluted with 100 ml ethyl acetate and stirred for 5 min and let sit for 1 h. The solid was filtered and washed with ethyl acetate (about 50 ml) and the combined filtrate was concentrated to afford the depicted product as a light-yellow oil (2.5 g, 72%).

PREPARATION 14

3-N-methylamino)-2-fluoropropan-1-ol

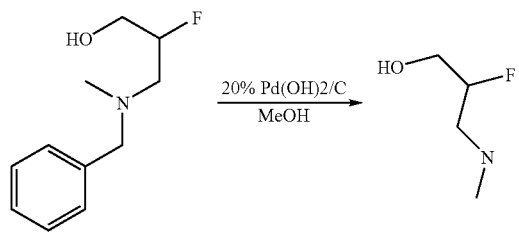

Twenty percent Pd(OH)$_2$ on carbon (200 mg) was added to Preparation 13 (2.5 g, 13 mmol) in 60 ml of methanol (MeOH). The mixture was hydrogenated at 60 PSI for 5 h. Solid was filtered off and the solution was concentrated to afford the depicted product as a light-yellow oil (1.4 g, ~100%).

PREPARATION 15

Carbobenzoxy-3-(N-methylamino)-2-fluoropropan-1-ol

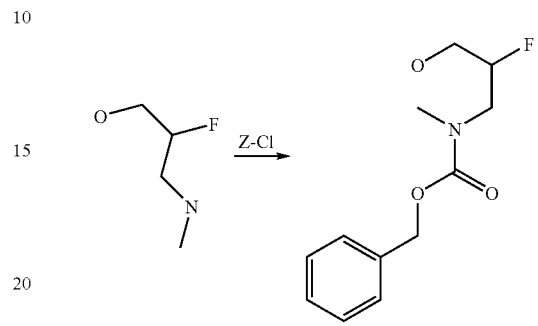

Diisopropylethylamine (DIEA) (2.2 g, 17 mmol) was added to Preparation 14 (1.4 g, 13 mmol) in 60 ml THF, followed by benzyl chloroformate (Z—Cl) (2.65 g, 15.6 mmol) drop wise at 0° C. The reaction was stirred at ambient temperature for 1 h and quenched by adding 30 ml 3 M hydrochloric acid (HCl). The mixture was stirred for 30 min at ambient temperature and extracted with ether (80 ml). The organic layer was washed with water (2×50 ml) and dried over MgSO$_4$ and concentrated to afford light-yellow oil. This crude oil was purified by chromatography (CombiFlash, ethyl acetate/hexane, 3% to 70%) to afford the depicted product as a clear oil (2.9 g, 95%).

PREPARATION 16

Carbobenzoxy-3-(N-methylamino)-2-fluoropropylphthalimide

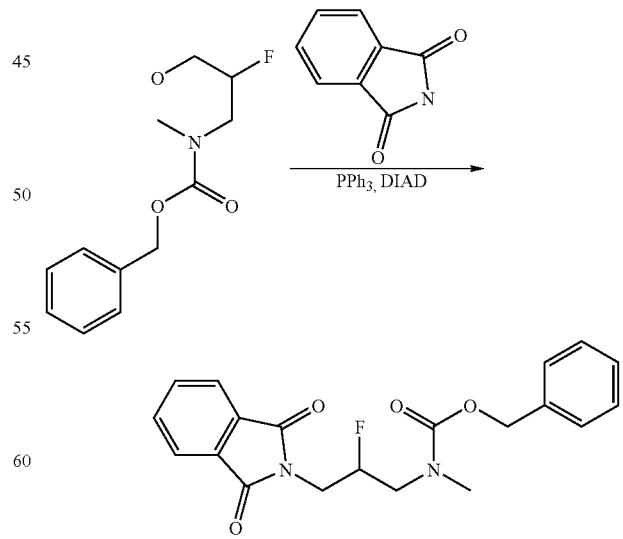

DIAD was added to a mixture of Preparation 15 (2.9 g, 12 mmol), phthalimide (2.1 g, 14.4 mmol), and Ph$_3$P (2.9 g, 14.4 mmol) in 60 ml THF at −20 C. The reaction mixture was then stirred at ambient temperature for 3 h. The reaction mixture was then diluted with ethyl acetate (60 ml), washed with brine (100 ml), dried over MgSO$_4$ and concentrated. The crude product was purified by chromatography (CombiFlash, ethyl acetate/hexane, 2% to 60%) to afford the depicted product as a sticky oil (3.5 g, 77%). This product contains a small amount of by-product generated from DIAD.

PREPARATION 17

Carbobenzoxy-3-(N-methylamino)-2,2-difluoropropylphthalimide

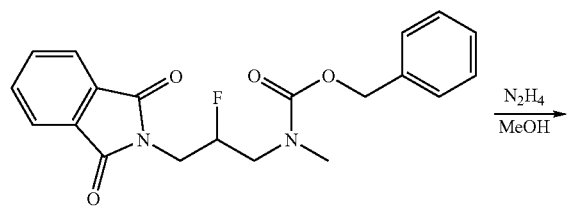

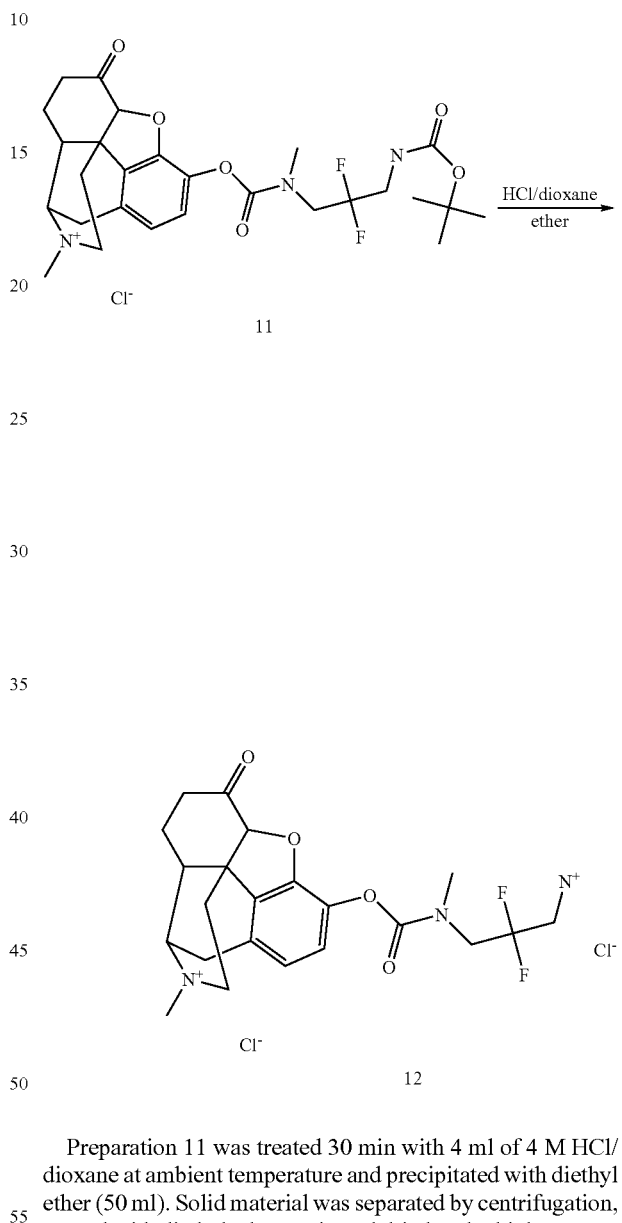

Preparation 16 (3.5 g, 9.4 mmol) was dissolved in 30 mL of MeOH followed by addition of hydrazine hydrate (1.8 g, 36 mmol). The mixture was stirred at 40° C. for about 20 min until the solution solidified. The mixture was let sit for 15 h and 50 ml of MeOH was added and mixed/stirred for 10 min. Solid was filtered off and the solution was concentrated. The residue was diluted with 100 ml of ether and let sit for 10 min. The mixture was filtered again and the filtrate was concentrated and acidified with 2 ml of acetic acid (AcOH). This material was submitted for reverse phase-HPLC. After purification, the trifluoroacetic acid (TFA) salt of the depicted compound was obtained as clear oil (2.44 g, 66%).

EXAMPLE 1

Hydromorphone 3-(N-methyl-N-(3-amino-2,2-difluoro)propyl)carbamate Hydrochloride Preparation 11 was treated 30 min with 4 ml of 4 M HCl/dioxane at ambient temperature and precipitated with diethyl ether (50 ml). Solid material was separated by centrifugation, treated with diethyl ether again and dried under high vacuum overnight to yield the depicted product, a white solid (0.18 g, 69%). Mass Spec: MH+=436.4. HPLC (Standard Post-purification Analytical Method): Retention Time 3.18 min.
Standard Post-purification Analytical Method
Column: Phenomenex Chromolith SpeedRod RP-18e C18 (4.6 mm×50 mm)
Flow-rate: 1.5 mL/min
Mobile Phase A: 100% water with 0.1% trifluoroacetic acid (TFA)
Mobile Phase B: 100% acetonitrile with 0.1% trifluoroacetic acid (TFA)

Gradient: 0% B to 60% B over 10.0 min, 60% B to 100% B over 0.2 min with a stay at 100% B for 1 min, then equilibration to 5% B over 0.8 min

EXAMPLE 2

Hydromorphone 3-(N-methyl-N-(3-amino-2-fluoro) propyl)carbamate Hydrochloride

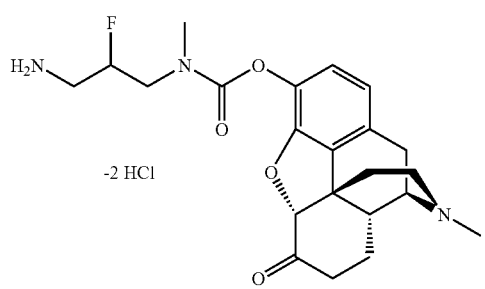

The depicted product was produced following a method similar to that described in Example 1 and Preparations 8 to 11 above, but starting from the product of Preparation 17: Boc-protection of Preparation 17 (0.5 g) yielded 273 mg (57%), Z-deprotection (removal of carboyl benzoxy group) yielded 90 mg (55%), coupling, and final purification yielded the depicted product (166 mg, 73%). Mass Spec: MH+=418.4. HPLC (Standard Post-purification Analytical Method—See Example 1): Retention Time 2.97 min.

PREPARATION 18

N-(3-methylaminopropyl)-trifluoroacetamide

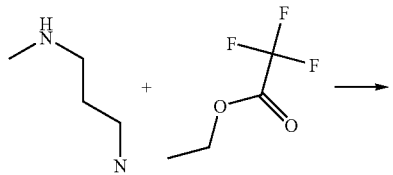

N-Methyl-1,3-diaminopropane (50 g, 0.56 mol) was dissolved in 200 mL acetonitrile followed by addition of ethyl trifluoroacetate (154 ml, 1.28 mol). The reaction mixture was stirred overnight at 85° C. The solvent was then removed in vacuo to yield the depicted product as a brown oil (101 g, 98.5%).

PREPARATION 19

N-(3-Cbz-methylaminopropyl)-trifluoroacetamide

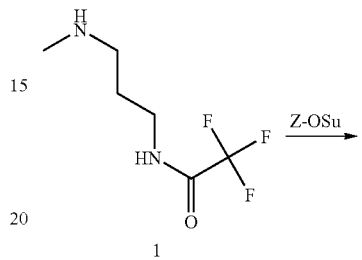

A portion of Preparation 18 (25 g, 0.1 mol) and Z-OSu were stirred at 45° C. for 2 h. The solvent was then removed under reduced pressure. The residue was treated with ethyl acetate (200 ml) and water (200 ml). The organic layer was washed with water, brine and dried over Na$_2$SO$_4$. The material was purified on silica gel (CombiFlash, 40 g column, hexane-ethylacetate), yielding the depicted product as a white solid (27.5 g, 86%).

PREPARATION 20

N-Boc-(3-Cbz-methylaminopropyl)-amine

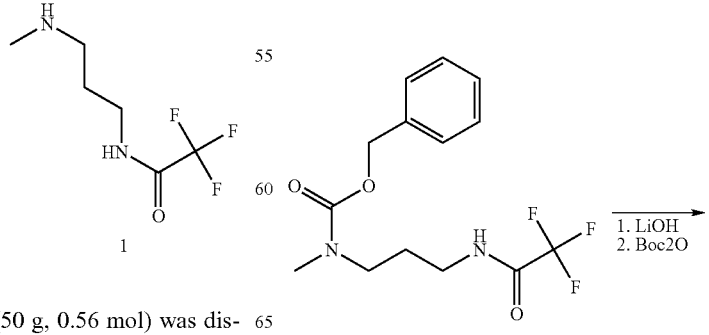

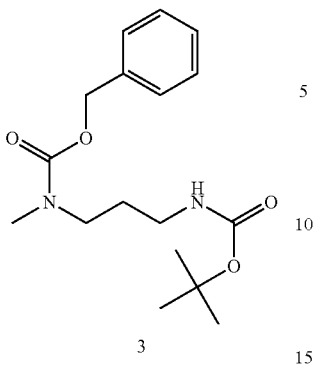

Preparation 19 (27.5 g, 0.086 mol) was treated by a mixture of LiOH (4.9 g), water (35 ml) and MeOH (350 ml) overnight at ambient temperature followed by addition of Boc$_2$O (18.6 g, 0.086 mol). The reaction mixture was stirred 5 h at ambient temperature. Volatiles were removed under reduced pressure. The residue was treated with ethyl acetate (200 ml) and water (200 ml). The organic layer was washed with water, brine and dried over Na$_2$SO$_4$. The material was purified on silica gel (CombiFlash, 40 g column, hexane-ethylacetate), yielding the depicted product as a white solid (12 g, 43%).

PREPARATION 21

N-Boc-(N'-methylaminopropyl)-amine

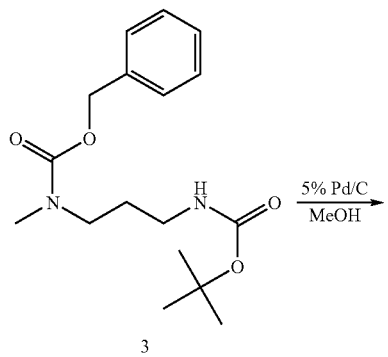

Preparation 20 (12 g, 0.037 mol) was hydrogenated 45 min in 100 ml of MeOH in the presence of 0.5 g of 5% Pd/C at 60 PSI of hydrogen. The catalyst was filtered off and the solvent was removed under reduced pressure to yield the depicted product as a colorless oil (6 g, 65%).

COMPARISON EXAMPLE

Hydromorphone
3-(N-methyl-N-(3-amino)propyl)carbamate
Hydrochloride

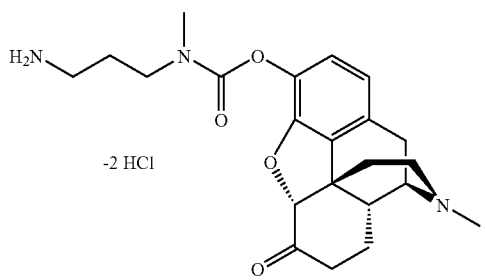

The depicted product was produced following the method of Example 1. Preparation 21 (188 mg) was coupled and purified to yield 249 mg (97%). Mass Spec: MH+=400.0. HPLC (Standard Post-purification Analytical Method—See Example 1): Retention Time 3.11 min.

Protocols for Evaluating Test Compounds

1. In Vitro Cyclization Assay

This assay measures the ability of a test compound of the present invention to cyclize in vitro. Also determined is the time required to effect such cyclization.

Test compounds are dissolved (approximately 2.2 mM) in 50 mM phosphate/citrate buffers at a variety of pHs, including pH 7.4 and pH 8.5. The disappearance of the test compounds is observed over time by incubating the solutions at 20° C. and periodically quantifying the concentration of the remaining compound. Since the rate of disappearance follows first order kinetics, the half-life of degradation is calculated from the slope of the regression of natural logarithm transformed data on time. For pH 10 half-life results, CPBG is used: The half-life assay is conducted in phosphate/citrate buffer to test compound stability at pH 6, pH 7.4 and pH 8.5, but citrate/phosphate/glycine buffer is used when compounds were tested at pH 10.

| Example | Nominal pH | Actual pH | Ave | SEM |
| --- | --- | --- | --- | --- |
| Comparison | 6 | 5.89 | 3,188.25 | 146.28 |
| Comparison | 7.4 | 7.22 | 223.57 | 1.57 |
| Comparison | 8.5 | 7.87 | 74.00 | 0.24 |
| Comparison | 10 | 9.68 | 1.33 | 0.18 |
| 2 | 6 | 5.87 | 334.34 | 10.07 |
| 2 | 7.4 | 7.2 | 18.10 | 0.00 |
| 2 | 8.5 | 7.75 | 5.18 | 0.07 |
| 2 | 10 | 9.7 | 1.68 | 0.27 |
| 1 | 6 | 5.89 | 99.09 | 1.13 |
| 1 | 7.4 | 7.2 | 9.43 | 0.02 |
| 1 | 8.5 | 7.81 | 6.13 | 0.01 |
| 1 | 10 | 9.69 | 8.04 | 0.08 |

Compounds according to the invention cyclize more rapidly than a compound lacking an electron-withdrawing substituent positioned beta to a nitrogen nucleophile.

The invention claimed is:

1. A compound of the general formula (I):

$$X-C(=O)-Y-R^1-NR^2R^3 \quad (I)$$

or a pharmaceutically acceptable salt thereof, in which:
X is a residue of a phenolic opioid selected from buprenorphine, dihydroetorphine, diprenorphine, etorphine, hydromorphone, levorphanol, morphine, nalmefene, naloxone, N-methylnaloxone, naltrexone, N-methylnaltrexone and oxymorphone in which the hydrogen atom of the phenol group is replaced by a covalent bond to $C(=O)-Y-R^1-NR^2R^3$;
Y is O, S or $NR^4$;
$R^1$ is selected from $-CH(CH_2F)CH(CH_2F)-$; $-CH(CHF_2)CH(CHF_2)-$; $-CH(CF_3)CH(CF_3)-$; $-CH_2CH(CF_3)-$; $-CH_2CH(CHF_2)-$; $-CH_2CH(CH_2F)-$; $-CH_2CH(F)CH_2-$; $-CH_2C(F_2)CH_2-$; $-CH(CH_2F)CH_2CH(CH_2F)-$; $-CH(CHF_2)CH_2CH(CHF_2)-$; $-CH(CF_3)CH_2CH(CF_3)-$; $-CH_2CH_2CH(CF_3)-$; $-CH_2CH_2CH(CHF_2)-$; and $-CH_2CH_2CH(CH_2F)-$;
$R^2$ is hydrogen or (1-4C)alkyl;
$R^3$ is an L-arginine or L-lysine residue or an N-acyl derivative thereof, or is a peptide, or an N-acyl derivative of the peptide, wherein the residue of the peptide bonded to N is an L-arginine or L-lysine residue; and
$R^4$ is hydrogen or (1-4C)alkyl;
wherein a digestive enzyme mediates release of X when the compound is administered to a patient.

2. A compound as claimed in claim 1, in which Y is $NR^4$.

3. A compound as claimed in claim 2, in which $R^4$ is methyl.

4. A compound as claimed in claim 2, in which $R^2$ is hydrogen.

5. A compound as claimed in claim 2, in which $R^3$ is a peptide or an N-acyl derivative thereof.

6. A compound as claimed in claim 5, in which $R^3$ is a dipeptide or tripeptide.

7. A compound as claimed in claim 1, in which $R^3$ is L-arginine, N-acetylarginine, N-glycinylarginine, N-acetylglycinylarginine, L-lysine, or N-acetyllysine.

8. A compound as claimed in claim 1, in which $R^3$ is a residue of L-lysine or L-arginine, or an N-acetyl or N-benzoyl derivative thereof.

9. A compound as claimed in claim 1, in which the phenolic opioid is selected from buprenorphine, dihydroetorphine, etorphine, hydromorphone, levorphanol, morphine and oxymorphone.

10. A compound as claimed in claim 1, in which the phenolic opioid is hydromorphone, morphine or oxymorphone.

11. A pharmaceutical composition, which comprises a compound as claimed in claim 1 and a pharmaceutically acceptable carrier.

12. A method of treating pain in a patient in need of treatment, which comprises administering an effective amount of a compound as claimed in claim 9.

13. A process for the preparation of a compound as defined in claim 1, which comprises:
a) reacting a compound of formula (II)

$$X-C(=O)-Z \quad (II)$$

or a protected derivative thereof, in which Z represents a leaving atom or group, with a compound of formula (III)

$$H-Y-R^1-NR^2R^3 \quad (III)$$

or a protected derivative thereof; or
b) reacting a compound of formula (IV)

$$X-C(=O)-Y-R^1-NHR^2 \quad (IV)$$

or a protected derivative thereof, with a compound of formula (V)

$$HR^3 \quad (V)$$

or a protected derivative thereof, or reactive derivative of said compound of formula (V) or protected derivative thereof;
followed, if desired, by N-acylating an amino group in $R^3$ to afford another compound of formula (I);
removing any protecting groups and, if desired, forming a pharmaceutically acceptable salt.

14. A method of providing a patient with post administration-activated, controlled release of a phenolic opioid comprising administering to said patient a compound according to claim 1.

15. A compound as claimed in claim 1, in which $R^4$ is methyl.

16. A compound as claimed in claim 2, in which the phenolic opioid is selected from buprenorphine, dihydroetorphine, etorphine, hydromorphone, levorphanol, morphine and oxymorphone.

17. A method of treating pain in a patient in need of treatment, which comprises administering an effective amount of a compound as claimed in claim 16.

18. A compound as claimed in claim 2, in which the phenolic opioid is hydromorphone, morphine or oxymorphone.

19. A pharmaceutical composition which comprises a compound as claimed in claim 2 and a pharmaceutically acceptable carrier.

20. A method as claimed in claim 14, in which Y is $NR^4$.

21. A method as claimed in claim 20, in which $R^2$ is hydrogen.

* * * * *